United States Patent [19]
Broemer et al.

[11] 3,981,736
[45] Sept. 21, 1976

[54] BIOCOMPATIBLE GLASS CERAMIC MATERIAL

[75] Inventors: Heinz Broemer, Hermannstein; Hans-Herbert Kaes, Wetzlar-Dorlar; Emanuel Pfeil, Marburg, all of Germany

[73] Assignee: Ernst Leitz G.m.b.H., Wetzlar, Germany

[22] Filed: May 12, 1975

[21] Appl. No.: 576,797

Related U.S. Application Data

[62] Division of Ser. No. 471,891, May 21, 1974, Pat. No. 3,922,155.

[30] Foreign Application Priority Data

May 23, 1973 Germany............................ 2326100

[52] U.S. Cl.................................. 106/39.6; 3/1.9; 3/1.913; 106/52; 106/54; 128/92 C
[51] Int. Cl.².......................... A61F 1/00; C03C 3/22
[58] Field of Search...................... 106/39.6, 52, 54; 3/1.9, 1.913; 128/92 C, 92 CA

[56] References Cited
UNITED STATES PATENTS
3,787,900  1/1974  McGee .................................. 3/1.9

OTHER PUBLICATIONS

Hench, L. L. et al., J. Biomedical Mater. Res. Symposium No. 2 (Part 1) pp. 117–141 "Bonding Mechanisms at the Interface of Ceramic Prosthetic Materials," (1971).

Hench, L. L. et al., J. Biomedical Mater. Res. Symposium No. 4 pp. 25–42 "Direct Chemical Bond of Bioactive Glass–Ceramic Materials to Bone and Muscle" (1973).

*Primary Examiner*—Helen M. McCarthy
*Attorney, Agent, or Firm*—Erich M. H. Radde

[57] ABSTRACT

The glass ceramic material of the present invention has the following composition, in weight percent,:
  About 20 to about 60 percent of silicon dioxide $SiO_2$,
  about 5 to about 40 percent of phosphorus pentoxide $P_2O_5$,
  about 2.7 to about 20 percent of sodium oxide $Na_2O$,
  about 0.4 to about 20 percent of potassium oxide $K_2O$,
  about 2.9 to about 30 percent of magnesium oxide $MgO$, and
  about 5 to about 40 percent of calcium oxide $CaO$,
and may contain between
  about 0.5 and about 3.0 percent of fluorine.

The glass ceramic material is produced by melting the mixture of components and subjecting the resulting melt to a specific annealing or tempering treatment to cause formation of nuclei and ceramization. Such glass ceramic material is especially useful as bone and tooth replacement material in humans and animals.

4 Claims, 3 Drawing Figures

BIOCOMPATIBLE GLASS CERAMIC MATERIAL

This is a division, of application Ser. No. 471,891 filed May 21, 1974, now U.S. Pat. No. 3,922,155.

BACKGROUND OF THE INVENTION

1. Field of the Invention

The present invention relates to a novel and useful glass ceramic material, to a process for the manufacture thereof, and to the use of the resultant material, in particular, as bone replacement material.

2. Description of the Prior Art

For osteoplastics and osteosynthesis there are employed, in addition to bone transplants, also metals such as, for instance, silver and tantalum, metal compounds such as, for instance, the surgical alloy steel "Vitallium" or the chromium-cobalt alloy "Protasul 1", and plastics such as, for instance, polyethylene, methacrylates, or silicone rubber.

While this tolerance of the body for some of the said implants in the animal or human organism can be considered satisfactory, none of the said materials or the materials known or tried out up to the present time are able to grow together with the bone in the living organism.

As is known, the substance of animal or human bone consists essentially of hydroxyapatite ($Ca_5[(OH)(PO_4)_3]$) which is permeated, in an intimate mixture, by albuminoids (collagen). The great difference in chemical composition between the bone-replacement material and the bone itself is the reason why the synthetic bone-replacement materials known up to the present time do not grow together with the mass of the bone.

Therefore, up to now it has been only possible, by suitable shaping of the implant, to obtain a certain mechanical anchoring, as a result whereof the tissue close to the bone simply envelopes the replacement material. The contact thus produced between the artificial implant and the bone, however, always remains weak and in particular cannot be subjected to the usual forces or stresses.

It is already known that regeneration of bone substances proceeds from the mineral hydroxyapatite. This substance evidently acts here as point of attachment for the albuminoids of the bone substance. Starting from hydroxyapatite nuclei, a complete bone is thus regenerated and built up. At the same time, connections to and with the bone fragments which are still present are also formed, i.e. formation of callus takes place.

Now, in itself, it would be possible to use apatite in sintered form as bone-replacement material. This method would, however, have the definite disadvantage that in order to obtain sufficient initial stability of the prosthesis or prosthesis part, there would have to be introduced very large quantities of apatite which exceed by far the quantities required for the synthesis of a bone. Under such conditions, regeneration and final development of a bone replacement capable of bearing loads, however, will require too much time.

L. L. Hench, R. J. Splinter, T. K. Greenlee, and W. C. Allen have proposed, in an article entitled "Bonding mechanisms at the interface of ceramic prosthetic materials," the use, as bone replacement, of apatite-containing materials which, as such, possess sufficient strength properties, so that, upon their intergrowth, full load-bearing capacity is obtained immediately. In said article, there are proposed glass ceramic materials in which a sufficient number of apatite nuclei are produced by suitable thermal treatment, so that the growth of the bone can take place in a known manner on such nuclei. Thus it can be assumed with some degree of certainty that such a glass ceramic material will grow together with the existing bone in situ.

The glass ceramic materials proposed by Hench et al., however, have serious disadvantages which can cause their use in the animal or human oraganism to become a serious source of danger for the animal or person bearing the implant, especially when implanting large replacement pieces.

Since it is known that the ratio of the two ions $Na^+$ and $K^+$ to each other is a decisive factor for proper functioning of the nerves and muscles in the animal organism, even relatively small variations and displacements, in particular of the potassium ion concentration will change the excitability or responsiveness of the nerves and thus will lead to serious impairment of the heart. Said ratio of sodium to potassium ions is all the more important because the extracellular potassium ion concentration, which in general is the only important factor, constitutes only about 2 percent of the total potassium content of an organism. Disturbances in this small amount of extracellular material which, as a whole, constitutes only about 2 g. to 3 g. of potassium ions can be caused by even only relatively small shifts in the potassium content of the blood or lymph.

Similar considerations must also be made with respect to the $Mg^{2+}$ and $Ca^{2+}$ ions which are also present in the animal and human organism in a substantially invariable ratio and in a concentration which is also invariable. Changes and shifting of said ratio necessarily result in severe damage in the organism in question.

The glass ceramics proposed by Hench et al. are prepared from pure sodium-calcium glasses.

It is self-evident that, in view of the known capability of glass to act as ion exchanger, there exists a potential of sodium $Na^+$ ions and calcium $Ca^{2+}$ ions which, one the one hand, will greatly change, by leaching out, the concentration of these two ions at the area surrounding the glass ceramic implant and which, on the other hand, will also considerably reduce by exchange adsorption the concentration of the ion antagonists, for instance, of potassium $K^+$ ions and magnesium $Mg^{2+}$ ions. Thus it is to be expected that, when implanting larger replacement pieces, the effect on the specific ion concentration will extend, as a function of the geometric shape of the implant, to more remote organs and their functions. As a result thereof a high displacement of the ionic ratios is to be expected especially when the ceramics are used in the form of porous sintered or foam materials, i.e. in a form which is particularly favorable for technical-medical reasons.

Another substantial disadvantage of the known glass ceramics is their relatively low tendency to form nuclei. This leads to extremely long and technically expensive recrystallization processes. Furthermore, the number of nuclei formed per unit of volume is very difficult to control technologically since it is dependent on numerous imponderable factors such as the degree of purity of the chemical starting materials, the prior heat treatment or thermal antecedents of the glass, the material of which the crucible consists, the constancy of the heating program, and others.

SUMMARY OF THE INVENTION

It is one object of the present invention to provide a novel and useful glass ceramic material which does not have the disadvantages of the previously known bone-replacement materials, which, at the same time, has the apatite structure required for intimate intergrowth or fusion, and which, finally, is characterized by good compatibility with the organism.

Another object of the present invention is to provide a simple and effective process of producing such a useful glass ceramic material.

A further object of the present invention is to use such a novel glass ceramic material as bone-replacement material in humans and animals.

Other objects of the present invention and advantageous features thereof will become apparent as the description proceeds.

In principle these objects of the present invention are achieved by providing a glass ceramic material of the following composition, in weight percent:

About 20 to about 60 percent of silicon dioxide $SiO_2$,
about 5 to about 40 percent of phosphorus pentoxide $P_2O_5$,
about 2.7 to about 20 percent of sodium oxide $Na_2O$,
about 0.4 to about 20 percent of potassium oxide $K_2O$,
about 2.9 to about 30 percent of magnesium oxide MgO, and
about 5 to about 40 percent of calcium oxide CaO.
Such glass ceramic material may additionally contain between
about 0.05 to about 3.0 percent of fluorine $F_2$.

A preferred glass ceramic material of this type is composed (in weight percent) of the following components:

About 30 to about 60 percent of silicon dioxide $SiO_2$,
about 5 to about 20 percent of phosphorus pentoxide $P_2O_5$,
about 3 to about 10 percent of sodium oxide $Na_2O$,
about 3 to about 10 percent of potassium oxide $K_2O$,
about 5 to about 20 percent of magnesium oxide MgO, and
about 10 to about 30 percent of calcium oxide CaO.
Such a preferred glass ceramic material may additionally contain between
about 0.5 and about 2.5 percent of fluorine $F_2$.

The glass ceramic material according to the present invention is produced from a mixture consisting substantially of silicon dioxide $SiO_2$, sodium oxide $Na_2O$, potassium oxide $K_2O$, magnesium oxide MgO, a calcium phosphate, and, if desired, calcium fluoride $CaF_2$. The amounts of the components in said mixture are such that a glass ceramic material of the oxide and, if desired, fluorine composition as given hereinabove, is produced.

Preferably the glass ceramic material of the above given composition is obtained by melting down a mixture essentially consisting, in weight percent, of
about 20 to about 60 percent of silicon dioxide $SiO_2$,
about 2.7 to about 20 percent of sodium oxide $Na_2O$,
about 0.4 to about 20 percent of potassium oxide $K_2O$,
about 2.9 to about 30 percent of magnesium oxide MgO,
about 5 to about 25 percent of calcium oxide CaO, and
about 10 to about 30 percent of calcium orthophosphate $Ca_3(PO_4)_2$,
and subjecting the resulting melt to the following temperature-time ceramization program:

a. Heating the resulting molten and cooled glass to the temperature ($T_{KB}$) of optimum rate of crystal formation between about 550° C, and about 950° C. and maintaining said temperature ($T_{KB}$) for between about 8 hours and about 30 hours;

b. reducing the temperature of the mixture to a temperature ($T_0$) between about 350° C. and about 550°C. and maintaining said temperature ($T_0$) for between about 2 hours and about 5 hours;

c. increasing the temperature of the mixture to the temperature ($T_{KW}$) of optimum rate of crystal growth between about 700° C. and about 1150° C., and maintaining said temperature ($T_{KW}$) for between about 10 hours and about 40 hours; and d. cooling the mixture to room temperature.

The calcium orthophosphate $Ca_3(PO_4)_2$ of the starting mixture can be replaced by up to 25 percent of calcium metaphosphate $Ca(PO_3)_2$. In addition, the starting mixture may contain up to 5 percent of calcium fluoride $CaF_2$.

According to a preferred embodiment of the present invention a mixture composed of (in weight percent):
about 38.0 to about 47.3 percent of silicon dioxide $SiO_2$,
about 2.7 to about 12.0 percent of sodium oxide $Na_2O$,
about 0.4 to about 6.8 percent of potassium oxide $K_2O$,
about 2.9 to about 16.5 percent of magnesium oxide MgO,
about 10.0 to about 23.6 percent of calcium oxide CaO, and
up to about 25.5 percent of calcium orthophosphate $Ca_3(PO_4)_2$, or
up to about 18.4 percent of calcium metaphosphate $Ca(PO_3)_2$ and, if desired,
up to about 4.0 percent of calcium fluoride $CaF_2$ is subjected to the above described melting and annealing or tempering process.

In addition to, or in place of, calcium fluoride $CaF_2$, there may be added a corresponding equivalent amount of at least one other compound yielding fluorine ions such as sodium fluoride NaF, potassium fluoride KF, or magnesium fluoride $MgF_2$. Thereby, care must be taken that the fluorine content introduced into the glass ceramic material remains substantially the same.

The resulting glass ceramic material according to the present invention which, due to the specific temperature-time ceramizing melting program employed contains discrete crystallites in a glassy matrix, has proved to be useful, as pointed out hereinabove, for prosthetic purposes, i.e. for replacing bones or teeth. They can also be produced in porous sintered form or in the form of a foam material and can be used for other purposes.

BRIEF DESCRIPTION OF THE DRAWINGS.

The attached drawings serve to illustrate the present invention and will be described in detail hereinafter in connection with the description of the preferred embodiments of the present invention. In said drawings

DESCRIPTION OF THE PREFERRED EMBODIMENT

The present invention will be described more in detail in the following illustrative embodiments thereof without, however, being limited thereto. The composition of glass ceramic material according to the present invention is given in the following Table 1. The amounts of components are given therein in weight percent.

The following Table 1a corresponds to Table 1 whereby, however, the calcium orthophosphate and calcium oxide are given as CaO and $P_2O_5$.

is dissolved in 500 ml. of distilled water and the solution is sterilized at 121° C. in an autoclave for 15 minutes.

Figure 1:
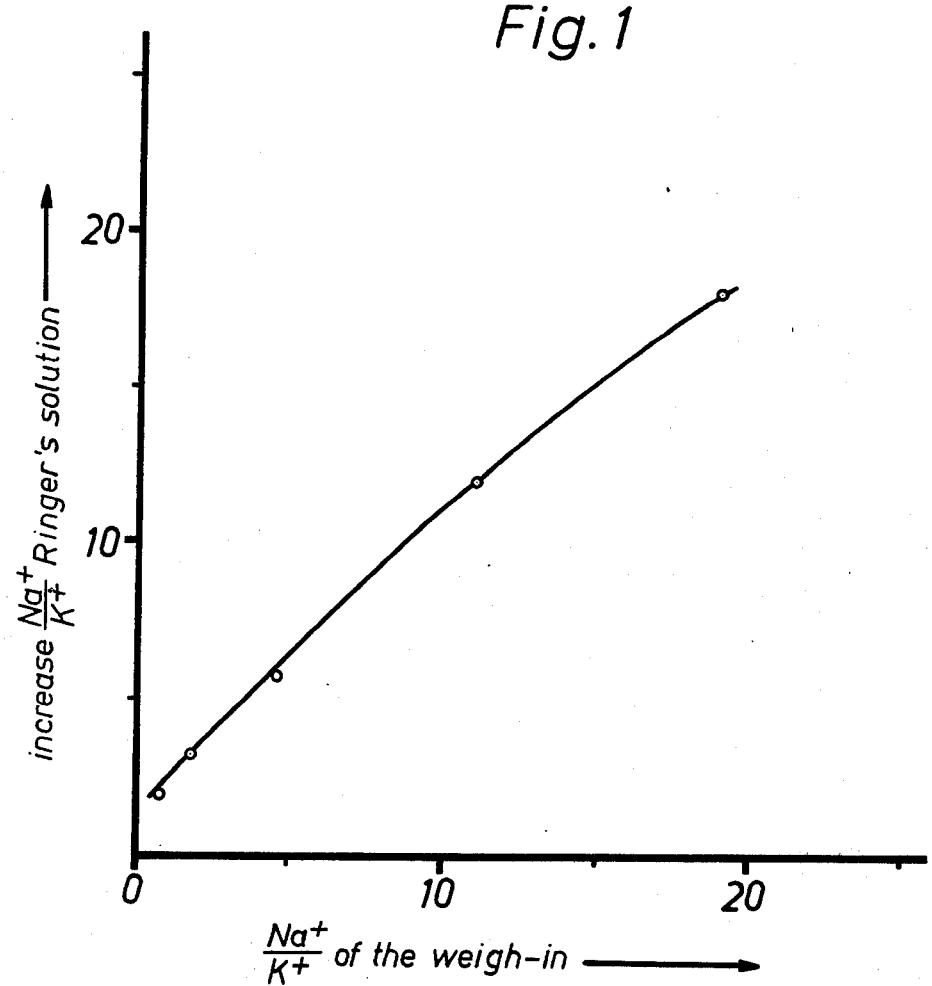
FIG. 1 shows a curve obtained on leaching out a preferred glass ceramic material according to the present invention with Ringer's solution and illustrates the increase in the $Na^+/K^+$ ratio in said solution as a function of the $Na^+/K^+$ ratio in the initial glass ceramic material.

The result of the leaching is shown in FIG. 1. The $NA^+/K^+$ ratio of the weighed portion of glass ceramic material is shown on the ordinate. The curve shows the increase in the $Na^+/K^+$ ratio in Ringer's solution as a function of the $Na^+/K^+$ ratio in the initial weighed sample of glass ceramic material after boiling under reflux for 6 ½ hours. FIG. 1 shows that by varying said ion ratio in the starting composition of the glass ceramic material, the optimum desired value in the solution corresponding to the optimum ratio for the respective organism into which the material is to be implanted can be achieved. Similar considerations apply also to the $Ca^{2+}/Mg^{2+}$ ratio, in which case, however, ion exchange processes must also be taken into account.

As a result of this treatment it was found that it was possible to produce glasses which, upon recrystallization, i.e. ceramization, exhibit an apatite structure but which, at the same time, - upon being leached by Ringer's solution - give off $Na^+$ and $K^+$ ions and $Ca^{2+}$ and $Mg^{2+}$ ions in the desired ratio.

TABLE 1

| Example No. | 1 | 2 | 3 | 4 | 5 (in weight %) | 6 | 7 | 8 | 9 | 10 | 11 |
|---|---|---|---|---|---|---|---|---|---|---|---|
| $SiO_2$ | 46.2 | 43.0 | 45.6 | 46.5 | 47.3 | 43.0 | 43.0 | 43.0 | 43.0 | 43.0 | 43.0 |
| $Ca_3(PO_4)_2$ | 25.5 | 21.0 | 22.3 | 22.7 | 23.2 | 21.0 | 21.0 | 21.0 | 21.0 | 21.0 | 21.0 |
| CaO | 20.2 | 16.0 | 16.0 | 16.0 | 16.0 | 15.0 | 14.0 | 13.0 | 12.0 | 11.8 | 11.0 |
| MgO | 2.9 | 7.0 | 7.0 | 7.0 | 7.0 | 8.0 | 9.0 | 10.0 | 11.0 | 11.5 | 12.0 |
| $Na_2O$ | 4.8 | 12.0 | 8.4 | 7.2 | 6.0 | 12.0 | 12.0 | 12.0 | 12.0 | 5.9 | 12.0 |
| $K_2O$ | 0.4 | 1.0 | 0.7 | 0.6 | 0.5 | 1.0 | 1.0 | 1.0 | 1.0 | 6.8 | 1.0 |

TABLE 1a

| Example No. | 1 | 2 | 3 | 4 | 5 (in weight %) | 6 | 7 | 8 | 9 | 10 | 11 |
|---|---|---|---|---|---|---|---|---|---|---|---|
| $SiO_2$ | 46.2 | 43.0 | 45.6 | 46.5 | 47.3 | 43.0 | 43.0 | 43.0 | 43.0 | 43.0 | 43.0 |
| $P_2O_5$ | 11.7 | 9.6 | 10.2 | 10.4 | 10.6 | 9.6 | 9.6 | 9.6 | 9.6 | 9.6 | 9.6 |
| CaO | 34.0 | 27.4 | 28.1 | 28.3 | 28.6 | 26.4 | 25.4 | 24.4 | 23.4 | 23.2 | 22.4 |
| MgO | 2.9 | 7.0 | 7.0 | 7.0 | 7.0 | 8.0 | 9.0 | 10.0 | 11.0 | 11.5 | 12.0 |
| $Na_2O$ | 4.8 | 12.0 | 8.4 | 7.2 | 6.0 | 12.0 | 12.0 | 12.0 | 12.0 | 5.9 | 12.0 |
| $K_2O$ | 0.4 | 1.0 | 0.7 | 0.6 | 0.5 | 1.0 | 1.0 | 1.0 | 1.0 | 6.8 | 1.0 |

A glass of the composition corresponding to that of Example 1 of Table 1, namely containing, in weight percent,:

46.2 % $SiO_2$,
25.5 % $Ca_3(PO_4)_2$,
20.2 % CaO,
2.9 % MgO,
4.8 % $Na_2O$, and
0.4 % $K_2O$, is recrystallized, i.e. subjected to the ceramization process described hereinabove and then is boiled under reflux in Ringer's solution for 6 ½ hours. The Ringer's solution is prepared in accordance with the following formula: One tablet consisting of 1.1250 g. NaCl
0.0525 g. KCl
0.0225 g. $CaCl_2$
0.0250 g. $NaHCO_3$ Predetermined and well-defined recrystallization or ceramization of the apatite structure in the glass ceramic material according to the present invention is favorably affected especially by an addition of calcium fluoride ($CaF_2$).

Table 2 shows the composition of mixtures of glass ceramic materials which contain $CaF_2$ and in which the calcium phosphate compound is either calcium orthophosphate $Ca_3(PO_4)_2$ or calcium metaphosphate $Ca(PO_3)_2$. Of course, such mixtures may also contain both said calcium phosphates alongside of each other.

The following Table 2a corresponds to Table 2 whereby, however, the calcium orthophosphate or metaphosphate and the calcium oxide are given as CaO and $P_2O_5$.

The following Table 3 shows the composition of additional glass ceramic materials with widely varying amounts of the main components while Table 3a corresponds to Table 3 whereby, however, the calcium orthophosphate or metaphosphate and the calcium oxide are given as CaO and $P_2O_5$.

TABLE 2

(in weight %)

| Example No. | 12 | 13 | 14 | 15 | 16 | 17 | 18 | 19 | 20 | 21 | 22 | 23 |
|---|---|---|---|---|---|---|---|---|---|---|---|---|
| $SiO_2$ | 43.0 | 38.0 | 38.0 | 38.0 | 46.0 | 43.0 | 43.0 | 43.0 | 46.0 | 43.0 | 43.0 | 43.0 |
| $Ca_3(PO_4)_2$ | — | — | — | — | — | — | — | — | — | — | 21.0 | 21.0 |
| $Ca(PO_3)_2$ | 13.4 | 18.4 | 13.4 | 13.4 | 13.4 | 16.4 | 13.4 | 13.4 | 13.4 | 13.4 | — | — |
| CaO | 18.6 | 18.6 | 18.6 | 23.6 | 18.6 | 18.6 | 18.6 | 21.6 | 18.6 | 18.6 | 11.0 | 10.0 |
| MgO | 11.5 | 11.5 | 16.5 | 11.5 | 11.5 | 11.5 | 14.5 | 11.5 | 11.5 | 11.5 | 11.5 | 10.5 |
| $Na_2O$ | 5.7 | 5.7 | 5.7 | 5.7 | 2.7 | 2.7 | 2.7 | 2.7 | 5.7 | 5.7 | 5.7 | 5.7 |
| $K_2O$ | 6.8 | 6.8 | 6.8 | 6.8 | 6.8 | 6.8 | 6.8 | 6.8 | 3.8 | 3.8 | 6.8 | 6.8 |
| $CaF_2$ | 1.0 | 1.0 | 1.0 | 1.0 | 1.0 | 1.0 | 1.0 | 1.0 | 1.0 | 4.0 | 1.0 | 3.0 |

TABLE 2a (in weight %)

| Example No. | 12 | 13 | 14 | 15 | 16 | 17 | 18 | 19 | 20 | 21 | 22 | 23 |
|---|---|---|---|---|---|---|---|---|---|---|---|---|
| $SiO_2$ | 43.0 | 38.0 | 38.0 | 38.0 | 46.0 | 43.0 | 43.0 | 43.0 | 46.0 | 43.0 | 43.0 | 43.0 |
| $P_2O_5$ | 9.6 | 13.2 | 9.6 | 9.6 | 9.6 | 11.8 | 9.6 | 9.6 | 9.6 | 9.6 | 9.6 | 9.5 |
| CaO | 22.4 | 23.8 | 22.4 | 27.4 | 22.4 | 23.2 | 22.4 | 25.4 | 22.4 | 22.4 | 22.4 | 21.4 |
| MgO | 11.4 | 11.5 | 16.5 | 11.5 | 11.5 | 11.5 | 14.5 | 11.5 | 11.5 | 11.5 | 11.5 | 10.5 |
| $Na_2O$ | 5.7 | 5.7 | 5.7 | 5.7 | 2.7 | 2.7 | 2.7 | 2.7 | 5.7 | 5.7 | 5.7 | 5.7 |
| $K_2O$ | 6.8 | 6.8 | 6.8 | 6.8 | 6.8 | 6.8 | 6.8 | 6.8 | 3.8 | 3.8 | 6.8 | 6.8 |
| $CaF_2$ | 1.0 | 1.0 | 1.0 | 1.0 | 1.0 | 1.0 | 1.0 | 1.0 | 1.0 | 4.0 | 1.0 | 3.0 |

TABLE 3

(in weight %)

| Example No. | 24 | 25 | 26 | 27 | 28 | 29 |
|---|---|---|---|---|---|---|
| $SiO_2$ | 20.0 | 42.0 | 45.0 | 20.0 | 40.0 | 60.0 |
| $Ca(PO_3)_2$ | 55.6 | 20.9 | 13.9 | — | — | — |
| $Ca(PO_4)_2$ | — | — | — | 63.5 | 26.4 | 10.9 |
| CaO | 13.4 | 9.1 | 1.1 | 5.5 | 5.6 | 10.1 |
| MgO | 5.0 | 5.0 | 30.0 | 5.0 | 5.0 | 5.0 |
| $Na_2O$ | 3.0 | 20.0 | 5.0 | 3.0 | 3.0 | 11.0 |
| $K_2O$ | 3.0 | 3.0 | 5.0 | 3.0 | 20.0 | 3.0 |

TABLE 3a (in weight %)

| Example No. | 24 | 25 | 26 | 27 | 28 | 29 |
|---|---|---|---|---|---|---|
| $SiO_2$ | 20.0 | 42.0 | 45.0 | 20.0 | 40.0 | 60.0 |
| $P_2O_5$ | 40.0 | 15.0 | 10.0 | 29.0 | 12.0 | 5.0 |
| CaO | 29.0 | 15.0 | 5.0 | 40.0 | 20.0 | 16.0 |
| MgO | 5.0 | 5.0 | 30.0 | 5.0 | 5.0 | 5.0 |
| $Na_2O$ | 3.0 | 20.0 | 5.0 | 3.0 | 3.0 | 11.0 |
| $K_2O$ | 3.0 | 3.0 | 5.0 | 3.0 | 20.0 | 3.0 |

Formation of nuclei, i.e. nucleation upon the addition of calcium fluoride $CaF_2$ can be illustrated quite graphically on the basic of a few examples of the composition of glass ceramic material mixtures.

In the following Table 4 there are given three examples taken from Tables 1 and 2.

TABLE 4

(in weight %)

Figure 2:
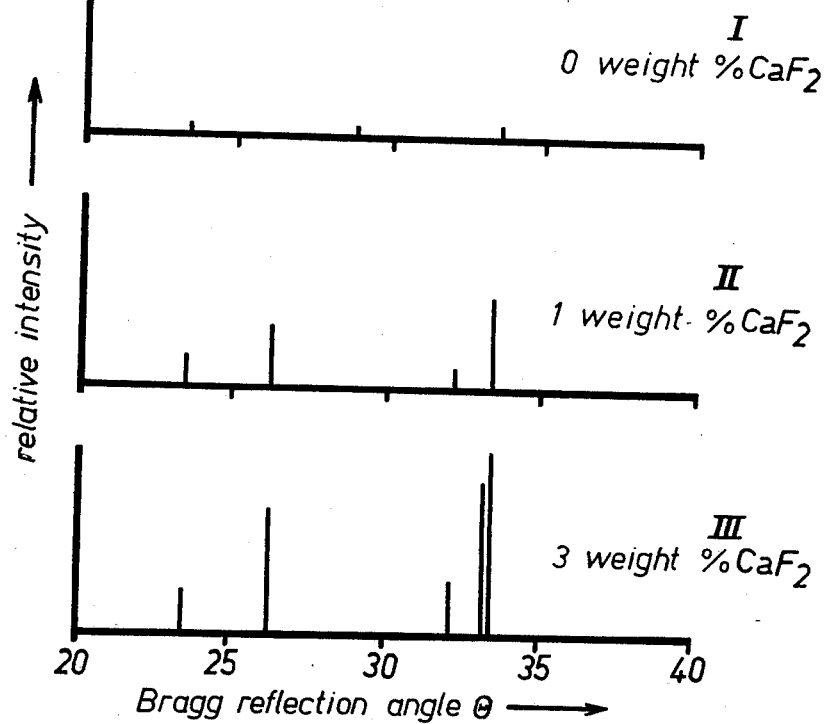
FIG. 2 shows diagrammatically the line diagrams of X-ray diffractometer pictures of certain glass ceramic materials according to the present invention with varying calcium fluoride content.

| | From Table 1 | From Table 2 | |
|---|---|---|---|
| Indicated in FIG. 2 by: | Example No. 10 — I | Example No. 22 — II | Example No. 23 — III |
| $SiO_2$ | 43.0 | 43.0 | 43.0 |
| $Ca_3(PO_4)_2$ | 21.0 | 21.0 | 21.0 |
| CaO | 11.8 | 11.0 | 10.0 |
| MgO | 11.5 | 11.5 | 10.5 |
| $Na_2O$ | 5.9 | 5.7 | 5.7 |
| $K_2O$ | 6.8 | 6.8 | 6.8 |
| $CaF_2$ | — | 1.0 | 3.0 |
| Structure determined by X-ray examination: | Very slight crystallization; crystals not identifiable | Definite crystallizaton of apatite | Very strong crystallization of apatite |

In FIG. 2 are shown diagrammatically the line diagrams obtained from X-ray diffractometer pictures of glass ceramic materials which were obtained from the illustrative mixtures as set forth under Nos. I to III in Table 4 hereinabove. In each case the height of the discrete lines is a measure of the relative intensity of the corresponding peaks and the latter in their turn are a measure of the degree of crytallinity of the respective mineral component. The X-ray pictures were made under the following conditions:

| | |
|---|---|
| X-radiation | CuKa |
| Wavelength | 1.5418 a |
| Filter | Ni |
| Voltage | 40 kV |

Within a $\theta$ range of about 23° to 34° ($\theta$ Bragg's reflection angle or glancing angle) all characteristic peaks were observed. The diagrams could be identified with the aid of the ASTM file.

In the upper part I of FIG. 2 representing Example I of Table 4 there are indicated only three lines of low intensity which do not yet permit a reliable determination and characterization of the structure of the material. While said Example I does not contain calcium fluoride $CaF_2$, the central part II of FIG. 2 representing Example II of Table 4 illustrates a material which additionally contains 1 percent by weight of calcium fluoride $CaF_2$. Said material was subjected to the same temperature-time ceramization treatment as Example I. As is evident, characteristic lines appear which render possible their identification as apatite. Finally part III of FIG. 2 corresponding to Example III of Table 4 is a photographic picture of a material obtained from a mixture containing additionally 3 percent by weight of calcium fluoride $CaF_2$. The resulting diffractometer diagram is quite pronounced and clearly indicates the presence of the mineral component apatite.

These diagrams thus clearly prove that addition of a fluoride, i.e. of calcium fluoride $CaF_2$, to the mixture, when the specific temperature-time ceramization program according to the present invention is maintained, yields a crystal phase with apatite structure in the glass ceramic matrix. The result of the evaluation of the diagram shown in FIG. 2 is given in Table 5.

TABLE 5

| Bragg angle [°] | d-Values [A] | Miller Indices [hkl] | Designation of the mineral component | ASTM File No. |
|---|---|---|---|---|
| 33.4 | 2.68 | 300 | carbonate apatite (Dahlite) | 13 - 1 |
| 33.3 | 2.69 | 300 | carbonate apatite | 19 - 272 |
| 32.3 | 2.77 | 142 | carbonate apatite (Dahlite) | 13 - 1 |
| 32.2 | 2.78 | 211/112 | carbonate apatite | 19 - 272 |
| 28.8 | 3.07 | 001 | $CaO \cdot SiO_2$ | 9 - 210 |
| 26.2 | 3.40 | 002 | carbonate apatite | 19 - 272 |
| 23.4 | 3.80 | — | Nagelschmidtite | 5 - 0646 |

It must be emphasized that identification of the mineral compounds indicated permits to make the general, crystallographically established statement that examination of the samples of materials proves the generation of an apatite crystal lattice structure, since a relationship of isotropy or at least an isotypic relationship exists between the carbonate apatite bearing the mineral name Dahlite (ASTM File No. 13 - 1) or the carbonate apatite (ASTM File No. 19 - 272) and, for instance, the hydroxy apatite or the fluorapatite.

Figure 3:
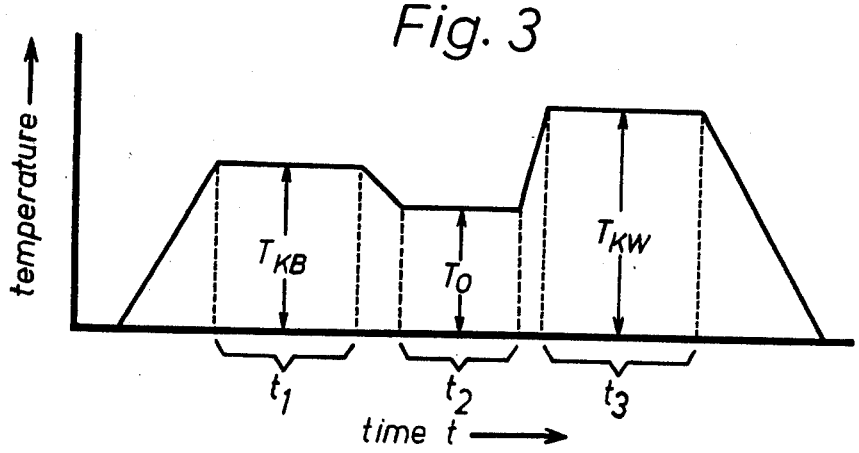
FIG. 3 illustrates diagrammatically the optimum temperature-time ceramization program as used in the process according to the present invention.

The optimum temperature-time ceramization program with regard to the process of the present invention is shown diagrammatically in FIG. 3. The abbreviations used in said FIG. 3 have the following meaning:

$T_{KB}$: Temperature of maximum speed of crystal formation;

$T_{KW}$: Temperature of maximum rate of crystal growth;

$T_O$: Setting temperature.

The ceramization process of the present invention is carried out at the following ceramization ranges of temperature and time:

$T_{KB}$ : Between about 550° C. and about 950° C.;
$T_{KW}$ : Between about 700° C. and about 1150° C.;
$T_O$ : Between about 350° C. an about 550° C.
$t_1$ : Between about 8 hours and about 30 hours;
$t_2$ : Between about 2 hours and about 5 hours;
$t_3$ : Between about 10 hours and about 40 hours.

Melting of the glass component mixture and subsequent annealing or ceramization are carried out as described hereinafter.

The glass component mixture is molten, for instance, in a platinum crucible at a temperature between about 1400° C. and about 1555° C. and preferably at about 1480° C. within about 3 to 4 hours. The molten mixture is then cooled to room temperature or to the temperature of the final ceramization or annealing step and is then subjected to the temperature-time ceramization program illustrated graphically in FIG. 3 so as to produce the glass ceramic material containing an apatite structure according to the present invention.

It may be mentioned that addition of minor amounts of boron trioxide $B_2O_3$ or other substances as they are conventionally used in glass engineering, with the exception of toxicologically effective compounds (such as beryllium oxide BeO, lead oxide PbO, and others) lies also within the scope of the present invention.

The use of the glass ceramic materials thus produced as partial or full replacement material for bones or teeth is especially suitable not only because of the above-indicated advantages such as compatibility with the body, possibility of completely growing together with the bones present in the body, and others, but also because these materials can readily be worked mechanically. Such glass ceramic materials can be cast into molds, they can be subjected to plastic deformation and can be compressed, cut, blown, milled, sawed, filed, drilled, and the like. As porous sintered or foam materials, a very high specific surface is obtained.

For instance, the glass ceramic material according to the present invention can be used for replacing knee joints which have become stiff due to rheumatoid arthritis or the like. It is possible to restore to a large extent proper functioning of such knee joints.

The same result with respect to their functioning is achieved by replacing hip joints or the head of the femur by such glass ceramic materials.

Said material has also been used successfully for replacing teeth by implanting it in suitably shaped form into the jaw bone. Preferably the prosthesis is fastened to the jaw bone by means of screws, needles, clamps, or the like. It is also possible to provide the shaped glass ceramic material with a thread so that it can be threaded into the jaw bone. Or it can be shaped like a dowel and dowelled into the jaw bone.

A complicated bone fracture can be repaired by removing the damaged part of the bone and inserting in its place a correspondingly shaped glass ceramic replacement part. Such a replacement part usually grows together at the places of contact with the natural bone material within three to six weeks.

According to another embodiment of the present invention the glass ceramic material can be distributed in the form of a powder upon the surface of a suitably shaped article composed of a conventional bone replacing material, for instance, upon the surface of a bone shaped article of aluminum oxide or a metallic replacement part. The thus coated article is then subjected to a temperature treatment to cause sintering or fusing together of the powder coating and forming a porous sintered and/or glaze-like surface layer. Said glass ceramic layer retains the outstanding properties of said material and especially its biocompatibility and, as a result thereof, the thus refined aluminum oxide or metal bone replacement part can readily be implanted in the body.

The glass ceramic material of the present invention and articles made therefrom can also be provided with pigments or dyes dispersed therein for certain decorative purposes.

It is furthermore possible to optimize the parameters of solid-state body mechanics by purposeful incorporation in the manner of fiber-reinforced materials. Thus, for instance, the weight of the bone implant can be reduced by producing a compact tubular glass ceramic material and providing its cavity with foam-like glass ceramic material of the same composition. Care must be taken thereby, however, that the mechanical strength and stability properties of the resulting bone implant are not substantially reduced and impaired.

We claim:

1. An apatite-containing glass ceramic material of satisfactory biocompatibility, said material being formed by thermal crystallization of a glass consisting essentially, in weight percent, of Between about 20 and about 60 percent of silicon dioxide $SiO_2$, between about 5 and about 40 percent of phosphorus pentoxide $P_2O_5$, between about 2.7 and about 20 percent of sodium oxide $Na_2O$,
between about 0.4 and about 20 percent of potassium oxide $K_2O$,
between about 2.9 and about 30 percent of magnesium oxide MgO, and
between about 5 and about 40 percent of calcium oxide CaO.

2. The material of claim 1, additionally containing between about 0.05 and about 3.0 percent of fluorine $F_2$.

3. The material of claim 1, essentially consisting, in weight percent, of:

Between about 30 and about 60 percent of silicon dioxide $SiO_2$,
between about 5 and about 20 percent of phosphorus pentoxide $P_2O_5$,
between about 3 and about 10 percent of sodium oxide $Na_2O$,
between about 3 and about 10 percent of potassium oxide $K_2O$,
between about 5 and about 20 percent of magnesium oxide MgO, and
between about 10 and about 30 percent of calcium oxide CaO.

4. The material of claim 3, additionally containing between about 0.5 and about 2.5 percent of fluorine $F_2$.

* * * * *

PO-1050
(5/69)

UNITED STATES PATENT OFFICE
CERTIFICATE OF CORRECTION

Patent No. 3,981,736                    Dated    September 21, 1976

Inventor(s) HEINZ BROEMER, HANS-HERBERT KAES, EMANUEL PFEIL

It is certified that error appears in the above-identified patent and that said Letters Patent are hereby corrected as shown below:

Column 1, line 20:  "this" should read -- the --.
Column 2, line 9:   "oraganism" should read -- organism --.
Column 6, line 5:   "NA$^+$/K$^+$" should read -- Na$^+$/K$^+$ --.
Column 6, line 56:  "Ca(-" should read -- Ca(PO$_3$)$_2$ --.
Column 6, line 57:  "PO$_3$)$_2$" should be cancelled.
Column 7, Table 3:  "Ca(PO$_4$)$_2$" should read -- Ca$_3$(PO$_4$)$_2$.
Column 7, line 48:  "basic" should read -- basis --.
Column 8, line 36:  "CuKa" should read -- CuK$_\alpha$ --.
Column 8, line 37:  "1.5418 a" should read -- 1.5418 Å --.
Column 8, line 42:  "$\vartheta$ Bragg's" should read -- $\vartheta$ = Bragg's --.

Signed and Sealed this

First Day of February 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,981,736   Dated September 21, 1976

Inventor(s) HEINZ BROEMER, HANS-HERBERT KAES, EMANUEL PFEIL

It is certified that error appears in the above-identified patent and that said Letters Patent are hereby corrected as shown below:

Cover page, In the Abstract, line 15 should read:

"about 0.05 and about 3.0 percent of fluorine."

Signed and Sealed this ninth Day of August 1977

[SEAL]

Attest:

RUTH C. MASON
*Attesting Officer*

C. MARSHALL DANN
*Commissioner of Patents and Trademarks*